(12) United States Patent
Iyer et al.

(10) Patent No.: US 6,531,589 B1
(45) Date of Patent: *Mar. 11, 2003

(54) BASE PROTECTING GROUPS AND SYNTHONS FOR OLIGONUCLEOTIDE SYNTHESIS

(75) Inventors: Radhakrishnan P. Iyer, Shrewsbury; Theresa Devlin, Jamaica Plain; Ivan Habus, Shrewsbury; Dong Yu, Shrewsbury; Sudhir Agrawal, Shrewsbury; Nan-Hui Ho, Shrewsbury, all of MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/598,320

(22) Filed: Feb. 8, 1996

Related U.S. Application Data

(63) Continuation-in-part of application No. 08/518,921, filed on Aug. 24, 1995, now Pat. No. 5,614,622, which is a continuation-in-part of application No. 08/457,198, filed on Jun. 1, 1995.

(51) Int. Cl.$^7$ .............................................. C07H 21/00
(52) U.S. Cl. ................. 536/25.31; 536/25.33; 536/25.34; 536/26.7; 536/26.71; 536/26.72; 536/26.74; 536/26.8; 536/26.9; 536/27.6; 536/27.62; 536/27.8; 536/27.81; 536/28.5; 536/28.53
(58) Field of Search ............................ 536/25.31, 25.33, 536/25.34, 26.7, 26.71, 26.72, 26.74, 26.8, 26.9, 27.6, 27.62, 27.8, 27.81, 28.5, 28.53; 564/204

(56) References Cited

U.S. PATENT DOCUMENTS

| | | | | |
|---|---|---|---|---|
| 4,415,732 A | * | 11/1983 | Caruthers et al. | 536/25.34 |
| 5,264,566 A | | 11/1993 | Froehler et al. | 536/25.34 |
| 5,614,622 A | * | 3/1997 | Iyer et al. | 536/25.33 |
| 5,955,599 A | * | 9/1999 | Iyer, II et al. | 536/25.3 |
| 5,962,674 A | * | 10/1999 | Iyer, III et al. | 536/25.34 |

FOREIGN PATENT DOCUMENTS

| | | |
|---|---|---|
| NL | 8700724 | 10/1988 |
| WO | WO 93/08296 | 4/1993 |

OTHER PUBLICATIONS

Goodchild, "Conjugates of Oligonucleotides and Modified Oligonucleotides: A Review of Their Synthesis and Properties," *Bioconjugate Chemistry*, 1(3), 165–186 (1990); see p. 166, Scheme 1.*
Sonveaux, "The Organic Chemistry Underlying DNA Synthesis," *Bioorganic Chemistry*, 14, 274–325 (1986).*
*Aldrich Catalog/Handbook of Fine Chemicals*, 1984–85, Aldrich Chemical Co., Milwaukee, WI, 1984, see p. 858, 6th entry.*
Oh et al., "Effect of Retinoyladenine (a Retinoid) on the Differentiation of HL–60 Cell," *Korean J. Biochem.*, 26(1), 39–45 (1994).*
Iyer et al., "Methyl Phosphotriester Oligonucleotides: Facile Synthesis Using N–Pent–4–enoyl Nucleoside Phosphoramidites," *J. Organic Chem.*, 60(25), 8132–8133 (Dec. 15, 1995).*
Debenham et al., "Two New Orthogonal Amino–Protecting Groups That Can Be Cleaved under Mild or Neutral Conditions," *J. Amer. Chem. Soc.*, 117(11), 3302–3303 (1995).*
Madsen et al., "The Pent–4–enoyl Group: A Novel Amino–Protecting Group That is Readily Cleaved under Mild Conditions," *J. Organic Chem.*, 60(24), 7920–7926 (Dec. 1, 1995).*
Lopez et al., "n–Pentenoyl Esters versus n–Pentenyl Glycosides. Synthesis and Reactivity in Glycosidation Reactions," *J. Chem. Soc., Chem. Comm.*, (3), 159–161 (Feb. 1, 1991).*

* cited by examiner

*Primary Examiner*—James O. Wilson
*Assistant Examiner*—L. Eric Crane
(74) *Attorney, Agent, or Firm*—Hale and Dorr LLP

(57) ABSTRACT

The invention provides new methods for synthesizing oligonucleotides that allow for deprotection of the oligonucleotides under more mild conditions than existing methods. The invention further provides a nucleoside base protecting group that is stable under oligonucleotide synthesis conditions, but which can be removed under more mild conditions than existing protecting groups, as well as nucleoside synthons having such base protecting groups.

37 Claims, 1 Drawing Sheet

BASE PROTECTING GROUPS AND SYNTHONS FOR OLIGONUCLEOTIDE SYNTHESIS

This is a continuation-in-part of U.S. Ser. No. 08/518,921, filed Aug. 24, 1995, now U.S. Pat. No. 5,614,622 which is a continuation-in-part of U.S. Ser. No. 08/457,198, filed Jun. 1, 1995.

BACKGROUND OF THE INVENTION

1. Field of the Invention

The invention relates to the chemical synthesis of oligonucleotides and to chemical entities useful in such synthesis.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g.,*Methods in Molecular Biology, Vol 20: Protocols for oligonucleotides and Analogs* pp. 165–189 (S. Agrawal, Ed., Humana Press, 1993); *Oligonucleotides and Analogues: A Practical Approach,* pp. 87–108 (F. Eckstein, Ed., 1991); and Uhlmann and Peyman, supra. Agrawal and Iyer, *Curr. Op. in Biotech.* 6, 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron Lett.* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22, 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), teaches synthesis of oligonucleotide methylphosphonates using phosphoramidite chemistry. Connolly et al., *Biochemistry* 23, 3443 (1984), discloses synthesis of oligonucleotide phosphorothioates using phosphoramidite chemistry. Jager el al., *Biochemistry* 27, 7237 (1988), discloses synthesis of oligonucleotide phosphoramidates using phosphoramidite chemistry. Agrawal et al., *Proc. Antl. Acad. Sci. USA* 85, 7079–7083 (1988), discloses synthesis of oligonucleotide phosphoramidates and phosphorothioates using H-phosphonate chemistry.

Solid phase synthesis of oligonucleotides by each of the foregoing methods involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group of the incoming nucleoside and the 5' hydroxyl group of the 5'-most nucleoside of the nascent, support-bound oligonucleotide.

Refinement of methodologies is still required, however, particularly when making a transition to large-scale synthesis (10 umol to 1 mmol and higher). See Padmapriya et al., *Antisense Res. Dev.* 4, 185 (1994). Several modifications of the standard phosphoramidite methods have already been reported to facilitate the synthesis (Padmapriya et al., supra; Ravikumar et al., *Tetrahedron* 50, 9255 (1994); Theisen et al., *Nucleosides & Nucleotides* 12, 43 (1994); and Iyer et al., *Nucleosides & Nucleotides* 14, 1349 (1995)) and isolation (Kuijpers et al. *Nucl. Acids Res.* 18, 5197 (1990); and Reddy et al., *Tetrahedron Lett.* 35, 4311 (1994)) of oligonucleotides.

The routine synthesis of oligonucleotides is presently carried out using various N-acyl protecting groups for the nucleoside bases, such as isobutyryl (for guanine), and benzoyl for adenine and cytosine. After the synthesis of the oligonucleotides is carried out using either phosphoramidite chemistry or H-phosphonate chemistry, the protecting groups are removed by treatment with ammonia at 55–60° C. for 5–10 hours. Using these protecting groups, PO oligonucleotides and other modified oligonucleotides can be synthesized. But in certain instances where modified oligonucleotides are functionalized with base-sensitive groups, the functionalities often get removed while the deprotection is being carried out. Examples of such base-sensitive modified oligonucleotides include, ribonucleoside-containing oligonucleotides, methylphosphotriester oligonucleotides, phosphoramides, etc. In particular, the large-scale synthesis of RNA which is required for the ribozyme-based therapeutic strategies presents special challenges due to two factors. These are, first, 3'-5'to 2'-5'internucleotide chain migration during preparation of nucleoside monomer precursors, during synthesis, and during removal of protecting groups from the RNA, and second, degradation of RNA. Use of classical protecting groups compounds these factors. For successful RNA synthesis, it is essential that the 2' hydroxyl protecting group remains intact until the final deprotection step and that following its removal, the 2' hydroxyl group does not attack the vicinal phosphodiester groups and thereby promote cleavage or migration of the internucleotidic linkages. In other applications of oligonucleotides, it is desirable to have oligonucleotides still bound to the solid support. Such completely deprotected oligonucleotides still bound to the solid support can be useful in a variety of applications such as those involving isolation of transcription factors and other factors or elements that interact with oligonucleotides. They are also useful for solid-phase PCR, investigation into nucleic acid protein interactions by, for example, NMR, creation and use of combinatorial libraries, screening of nucleic acid libraries, and solid support based hybridization probes (analogous to Southern and Northern blotting protocols). Creating such a support bound, deprotected oligonucleotide would be greatly aided by having a protecting group that could be removed by mild conditions that would not cleave the oligonucleotide from the support.

There is, therefore, a need for methods for oligonucleotide synthesis that allow for deprotection of the oligonucleotide under more mild conditions than existing methods. There is further a need for nucleoside synthons having new base protecting groups that are stable under oligonucleotide synthesis conditions, but which can be removed under more mild conditions than existing protecting groups.

BRIEF SUMMARY OF THE INVENTION

The invention provides new methods for synthesizing oligonucleotides that allow for deprotection of the oligonucleotide under more mild conditions than existing methods. The invention further provides a nucleoside base protecting group that is stable under oligonucleotide synthesis conditions, but which can be removed under more mild conditions than existing protecting groups, as well as nucleoside synthons having such base protecting groups.

In a first aspect, the invention provides a novel nucleoside base protecting group having the general structure I:

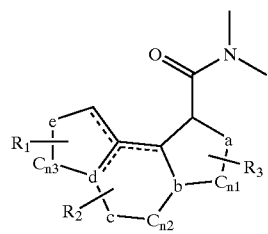

wherein $n_1$, $n_2$ and $n_3$ are each independently 0–10, wherein a, b, c, d and e are each independently hydrogen, carbon or nitrogen, and wherein the ring structure bearing substituent $R_3$ shown may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds. In a preferred embodiment, a is hydrogen when $n_1$ is 0 and is carbon or nitrogen when $n_1$ is 1–10, b is hydrogen when $n_1$ and $n_2$ are both 0 and is carbon or nitrogen when either or both $n_1$ and $n_2$ are 1–10, c is hydrogen when $n_2$ is 0 and is carbon or nitrogen when $n_2$ is 1–10, and e is hydrogen when $n_2$ is 0 and is carbon or nitrogen when $n_3$ is 1–10. In a particularly preferred embodiment, compound I has $n_1$, $n_2$ and $n_3$ values of 0, and a, b, c, d and e are each hydrogen, and the protecting group takes the form N-pent-4-enoyl, i.e., $CH_2=CH(CH_2)_2CO-$(II). Compounds I and II protect the nucleoside base amino moieties by forming amide linkages, as in:

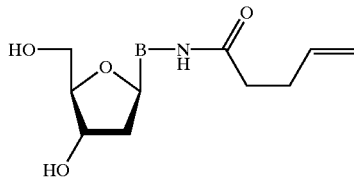

where the nitrogen displayed is the protected amino moiety of the base B.

Base protecting group I and the preferred embodiment II are particularly advantageously used because such protecting group can be removed chemoselectively by treatment with a chemoselective removing agent. Thus, in a second aspect, the invention provides a method for synthesizing oligonucleotides that allows for removal of base protecting groups under more mild conditions than existing methods. This new method comprises sequentially coupling nucleoside synthons having base protecting groups according to the invention to produce a base-protected oligonucleotide, followed by deprotection using a chemoselective removing agent. The method according to the invention can utilize any known or otherwise suitable oligonucleotide synthesis chemistry, including the well known H-phosphonate and phosphoramidite chemistries.

The use of this new method provides numerous advantages. For example the method's mild procedure for removing the protecting group without affecting the integrity of other functionalities present in the oligonucleotide makes it possible to prepare novel analogs of oligonucleotides such as ribonucleoside-containing oligonucleotides, alkylphosphotriesters, certain base-sensitive phosphoramidate and other base-sensitive oligonucleotides. Besides being able to synthesize oligonucleotides bearing "sensitive" functionalities, it can also be used in the routine synthesis of various oligonucleotides as in case of the conventional protecting groups. In addition, this new method allows for synthesis of oligonucleotides still bound to any type of solid support. Where an unprotected, support-bound oligonucleotide is desired, the full length support-bound oligonucleotide can have its internucleoside linkages oxidized, followed by contacting the oligonucleotide with a chemoselective removing agent to cleave the base protecting group.

A preferred use of this aspect of the invention is in the synthesis of RNA. Preferably, such synthesis employs a phosphoramidite, H-phosphonate or phosphotriester nucleoside monomer synthon having novel protecting groups according to the invention on the nucleoside base, as well as on the 2' hydroxyl of the nucleoside sugar.

DETAILED DESCRIPTION OF THE PREFERRED EMBODIMENTS

Figure 1:
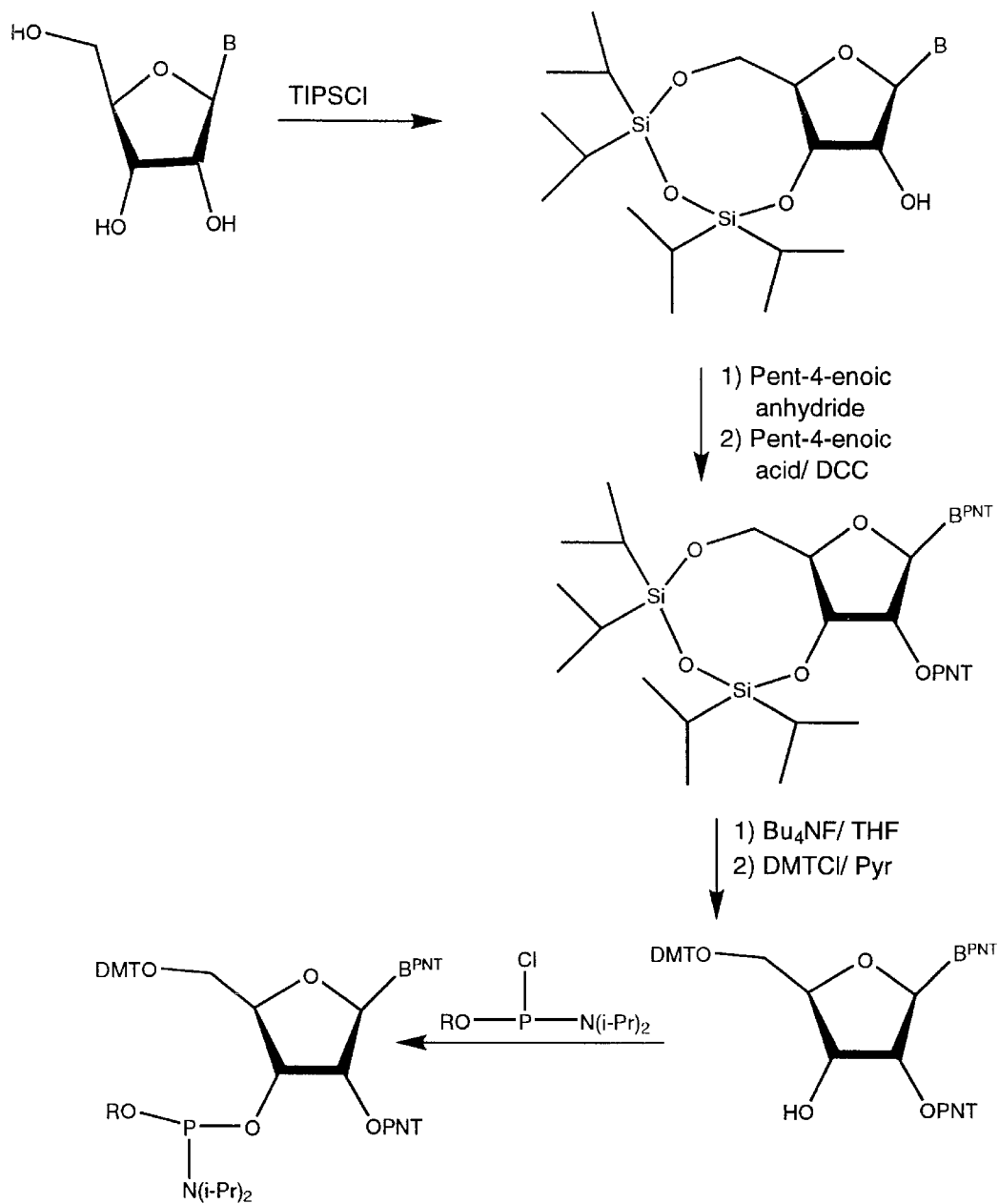
FIG. 1 shows a scheme for synthesis of RNA using the novel protecting group according to the invention (PNT). In this scheme, R is preferably $CH_3$ or $CH_3CH_2N$.

The invention relates to the chemical synthesis of oligonucleotides and to chemical entities useful in such synthesis. The patents and publications identified in this specification are within the knowledge of those skilled in this field and are hereby incorporated by reference in their entirety.

The invention provides new methods for synthesizing oligonucleotides that allow for deprotection of the oligonucleotide under more mild conditions than existing methods. The invention further provides a nucleoside base protecting group that is stable under oligonucleotide synthesis conditions, but which can be removed under more mild conditions than existing protecting groups, as well as nucleoside synthons having such base protecting groups.

In a first aspect, the invention provides a novel nucleoside base protecting group having the general structure I:

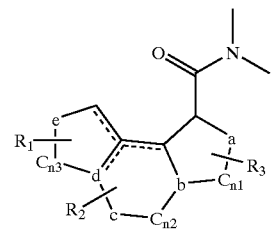

wherein $n_1$, $n_2$ and $n_3$ are each independently 0–10, wherein a, b, c, d and e are each independently hydrogen, carbon or nitrogen, and wherein the ring structure bearing substituent $R_3$ may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds (i.e., any one of the dotted double bonds is present). In a preferred embodiment, a is hydrogen when $n_1$ is 0 and is carbon or nitrogen when $n_1$ is 1–10, b is hydrogen when $n_1$ and $n_2$ are both 0 and is carbon or nitrogen when either or both $n_1$ and $n_2$ are 1–10, c is hydrogen when $n_2$ is 0 and is carbon or nitrogen when $n_2$ is 1–10, and e is hydrogen when $n_3$ is 0 and is carbon or nitrogen when $n_3$ is 1–10. In a particularly preferred embodiment, compound I has $n_1$, $n_2$ and $n_3$ values of 0, and a, b, c, d and e are each hydrogen, and the protecting group takes the form N-pent-4-enoyl, i.e., $CH_2=CH(CH_2)_2CO-$ (II). Compounds I and II protect the nucleoside base amino moieties by forming amide linkages, as in:

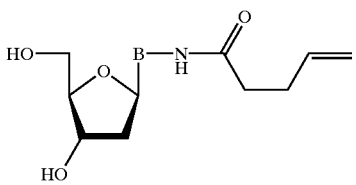

where the nitrogen displayed is the protected amino moiety of the nucleoside base B.

Base protecting group I and the preferred embodiment II are particularly advantageously used because such protecting groups can be removed chemoselectively by treatment with a chemoselective removing agent. Thus, in a second aspect, the invention provides a method for synthesizing oligonucleotides that allows for removal of base protecting groups under more mild conditions than existing methods. In this method, nucleoside synthons having base protecting groups according to the invention are sequentially coupled according to standard procedures to yield a base-protected oligonucleotide. The base protecting groups are then removed by a chemoselective removing agent. For purposes of the invention, a nucleoside synthon means a monomeric or multimeric nucleoside derivative appropriate for synthesis of an oligonucleotide. Preferred nucleoside synthons include monomeric nucleoside phosphoramidites, phosphotriesters, or H-phosphonates having a blocked 5'—OH, preferably blocked with a dimethoxytrityl group. A chemoselective removing agent means an agent that is capable of removing a base protecting group according to the invention. In certain preferred embodiments, the chemoselective removing agent is selected from the group consisting of halogens, especially $Br_2$, $Cl_2$ and $I_2$, any of which are preferably taken up in water, or in pyridine/ROH, wherein R is an alkyl, aralkyl or aryl group having 1–10 carbon atoms, or as an N-halosuccinimide. In alternative embodiments, non-chemoselective reagents may be used, such as aqueous ammonium hydroxide, alcoholic ammonia, alkali carbonates in organic solvents, primary or secondary amines, alkali hydroxides, or any amidolytic reagent, i.e., an agent capable of hydrolyzing an amide linkage.

This method can utilize any suitable oligonucleotide synthesis chemistry, including the well known H-phosphonate and phosphoramidite chemistries. In one preferred embodiment, synthesis is carried out on a suitable solid support using either H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon, Methods in Molec. Biol. 20: 465 (1993)). Synthesis on such a solid support begins with coupling a nucleoside synthon according to the invention to a nucleoside that is covalently linked the solid support (i.e., linked to a functionality on the solid support, preferably an amino or hydroxyl functionality). More generally, the method according to the invention can be used with any of the chemistries commonly used for oligonucleotide synthesis, whether in solution phase or in solid phase. Thus, the invention provides a method for synthesizing an oligonucleotide, the method comprising coupling suitable nucleoside synthon, such as a nucleoside H-phosphonate, a nucleoside phosphoramidite, or a nucleoside phosphotriester to a nucleoside and deprotecting a nucleoside base with a reagent comprising a halogen in water, or in pyridine/ROH, wherein R is an alkyl, aralkyl or aryl group having 1–10 carbon atoms. The nucleoside to which the nucleoside synthon is coupled may be a monomer, or it may be the terminal nucleoside of a growing oligonucleotide chain. In either case, the nucleoside or growing oligonucleotide chain may be support-bound or free in solution.

The versatility of chemical synthetic approach of the method according to the invention makes the method according to the invention suitable for the synthesis of any of a broad class of compounds, all of which are referred to herein as "oligonucleotides". For purposes of the invention, the term oligonucleotide includes polymers of two or more deoxyribonucleotide, or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group.

The use of this new method provides numerous advantages. For example the method's chemoselective capacity for removing the protecting group without affecting the integrity of other functionalities present in the oligonucleotide makes it possible to prepare novel analogs of oligonucleotides such as oligoribonucleotides, alkylphosphotriesters, certain base sensitive phosphoramidates and other base-sensitive oligonucleotides. Besides being able to synthesize oligonucleotides bearing "sensitive" functionalities, it can also be used in the routine synthesis of various oligonucleotides as in case of the conventional protecting groups. In addition, this new method allows for synthesis of oligonucleotides still bound to any type of solid support. Where an unprotected, support-bound oligonucleotide is desired, the full length support-bound oligonucleotide will have its internucleoside linkages oxidized, followed by contacting the oligonucleotide with a chemoselective removing agent to cleave the base protecting group. In the phosphoramidite approach, this is followed by treatment with anhydrous triethylamine to cleave the beta-cyanoethyl moiety.

Additionally, according to this aspect of the invention, support-bound branched oligonucleotides can be synthesized using, for example glycol residues in which one hydroxyl group is protected by e.g., DMT, and the other by a protecting group according to the invention. Then the DMT group may be selectively removed and an oligonucleotide synthesized from the resulting unprotected hydroxyl. Upon completion of that oligonucleotide, the hydroxyl moiety protected by the protecting group according to the invention can be deprotected with a chemoselective removing agent and another, different oligonucleotide synthesized from it.

A preferred use of this aspect of the invention is in the synthesis of RNA. Preferably, such synthesis employs a phosphoramidite, H-phosphonate or phosphotriester nucleoside monomer synthon having novel protecting groups according to the invention on the nucleoside base, as well as on the 2' hydroxyl of the nucleoside sugar. A scheme for synthesis of such a monomer having a particularly preferred embodiment of the protecting group according to the invention is shown in FIG. 1. According to this scheme, the monomer synthon is synthesized from the ribonucleoside by first protecting the 3' and 5' hydroxyl groups as the cyclic silyl ether derivative using the Markiewicz reagent. Then the N-pent-4-enoyl (PNT) group is installed at the nucleobase and the 2' hydroxyl of the ribose unit using PNT anhydride or using pent-4-enoic acid in the presence of dicyclohexylcarbodiimide (DCC). The 3' and 5' protecting groups are removed using tetrabutylammonium fluoride, followed by conversion of the diol to the 5'-O-4,4-dimethoxytrityl 3'-O-phosphoramidite monomer synthon by adaptation of standard phosphoramidite synthesis protocols using the appropriate chlorophosphitylation reagent. The monomer synthon according to the invention has the general structure:

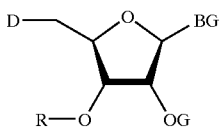

wherein B is a nucleoside base, D is a 5'—OH blocking group (see e.g. Sonveaux in *Methods in Molecular Biology, Vol 26: Protocols for Oligonucleotide Conjugates* pp. 28–36 (S. Agrawal, Ed., Humana Press, 1994), preferably dimethoxytrityl or trityl, the protecting group (G) is the previously described structure I, or its preferred embodiment II, and R is a phosphoramidite, H-phosphonate, or phosphotriester leaving group, including cyclic phosphoramidite leaving groups (see Iyer et al., J. Org. Chem. 60:5388–5389 (1995)). A minor isomerization product resulting from 2'-3' migration of groups is also formed, but is readily removed by chromatography. The formation of this minor product can also be substantially reduced by using bis-N,N-diisopropylphosphoramidite as the phosphitylating reagent.

Synthesis of RNA can be carried out using the monomer synthon according to the invention in standard RNA phosphoramidite chemistry with controlled-pore glass (CPG) as the solid support. Following synthesis, the protecting group is removed, preferably in I₂/pyridine/MeOH and the oligonucleotide is cleaved from the support, preferably using a solution of K₂CO₃/MeOH. 2'–5' product resulting from the migration of the 3'–5' internucleotidic linkage has not been detected based on enzymatic digestion of the RNA by ribonuclease T2 and spleen phosphodiesterase.

The following examples further illustrate certain preferred embodiments of the invention and are not limiting in nature.

EXAMPLE 1

Preparation of N-pent-4-enoyl 2'-deoxy Adenosine (dA Npr)

2'-Deoxyadenosine (Mallinkckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4 g, 20 mmol) was added and the contents stirred. After 15 min triethyl amine (3 ml) was added and the contents stirred for 2–3 h. The reaction slurry was cooled to 0–5° C. and 10 ml of water was added. After 5 min., 28% NH₄OH (10 ml) was added. The resulting clear solution was evaporated to dryness. Water (150 ml) was added and the reaction mixture was extracted with ethylacetate: ether (50 ml, 1:1). The aqueous layer was separated and concentrated to a small volume. Upon leaving at room temperature, a white precipitate of the title compound was obtained. Filtration and drying gave ca. 3.5 g of pure title compound. Several experiments repeating the above procedure, using larger scale of operation, gave the title compound in 85–90% yield.

The same general procedure can be employed for the preparation of dG and dC protected nucleosides.

EXAMPLE 2

Preparation of 5'-O-DMT-N-4-pent-4-enoyl-nucleoside Synthons

The title compound was prepared by adopting a procedure as described by Froehler in Protocols for Oligonucleotides and analogs, Agrawal, S. Ed., pp. 63–80 as given below:

To 544 mg (1.63 mmol) of dA(N-pr) in 20 ml of anhydrous pyridine was added 1.108 g (3.3 mmol) of dimethoxytritylchloride. The reaction mixture was stirred at room temperature for 12 h. The reaction mixture was evaporated to dryness. The residue was chromatographed over silica gel 60 and eluted with CH₂Cl2:CH₃OH:(Et)3N to give 0.73 of 5'-O-DMT-N-4-pent-4-enoyl-2'-deoxyadenosine as a white foamy material.

To a stirred solution of 1,2,4 triazole (0.944 g, 13.3 mmol) and triethylamine (5.5 ml, 30 mmol) in anhydrous CH₂Cl₂ (40 ml) was added PCl₃ (0.35 ml, 3.9 mmol) at room temperature under argon. After 30 min, the reaction mixture was cooled to 0° C. and 5'-DMT-protected nucleoside (500 mg, 0.88 mmol) in 15 ml CH₂Cl₂ was added dropwise over 10–15 min at 0° C. and allowed to warm to room temperature. The reaction mixture was poured into 1M triethylammoniumbicarbonate (TEAB) (75 ml, pH 8.5) with stirring. The mixture was transferred to a separatory funnel and the phases separated. The aqueous phase was extracted with methylene chloride and the combined organic phase washed with 1M TEAB (1×50 ml). The organic layer was dried over sodium sulfate and evaporated to dryness. The solid product thus obtained was purified by chromatography over silica gel. Elution with CH₂Cl₂:CH₃OH:(Et)₃N (18:1:1) gave 0.065 g of the title compound.

Other H-phosphonate nucleosides are similarly prepared in overall yields ranging from 70–90%.

Similarly nucleoside 5'-O-DMT-3'-6-cyanoethyl-N,N-diisopropylphosphoramidites and 5'+O-DMT-3'—N—N-diisopropylphosphoramidites were prepared using standard protocols as described by Beaucage, S. L., in Protocols for oligonucleotides and Analogs, Agrawal, S., Ed., pp. 33–61.

EXAMPLE 3

Solid Phase Coupling of Nucleoside Synthons and Removal of Base Protecting Groups Nucleoside synthons prepared according to Example 2 were coupled using solid phase H-phosphonate methodology (Froehler ref. above). The support bound oligonucleotide H-phosphonate was then treated with a solution of 2% $I_2$ in (pyridine:water, 98:2) for 30 min. This procedure completely removes the base protecting groups. An additional step to oxidize the H-phosphonate internucleoside linkages is not necessary if one is making oligonucleotide phosphodiesters using H-phosphonate methodology because simultaneous oxidation and deprotection can be achieved in a single reaction using the $I_2$ reagent specified above. Otherwise, conversion of the internucleoside linkage to phosphorothioates, morpholidates, or alkyltriesters is carried out according to standard procedures.

What is claimed is:

1. A monomer synthon having the structure:

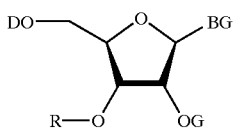

wherein B is a nucleoside base, D is a 5'-OH blocking group, R is a phosphoramidite, H-phosphonate or phosphotriester group, and G has the formula $CH_2=CH(CH_2)_2—C(O)—$, wherein G is attached by way of an amide linkage to the amino moiety of the nucleoside base B.

2. A method for synthesizing an oligonucleotide comprising:
sequentially coupling one or more monomer synthons according to claim 1 to a nucleoside to produce a base-protected oligonucleotide, wherein the R in the monomer synthon is an H-phosphonate, and then
deprotecting the base-protected oligonucleotide with a chemoselective agent comprising $Br_2$ or $I_2$ in water, or in pyridine/ROH, wherein the R in ROH is an alkyl, aralkyl or aryl group having 1–10 carbon atoms.

3. The method according to claim 2, wherein the R in ROH is a methyl group.

4. The method according to claim 2, wherein D is a dimethoxytrityl group.

5. The method of claim 2, wherein the method is conducted in a solution phase or a solid phase.

6. The method of claim 2, wherein the nucleoside is a monomer or a terminal nucleoside of an oligonucleotide chain.

7. The monomer synthon according to claim 1, wherein R is an H-phosphonate group.

8. A method for synthesizing an oligonucleotide comprising:
sequentially coupling a monomer synthon according to claim 1, to a nucleoside to produce a base-protected oligonucleotide, wherein the R in the monomer synthon is an H-phosphonate, and then
simultaneously oxidizing the internucleoside linkages and deprotecting the base-protected oligonucleotide with a chemoselective agent comprising $Br_2$ or $I_2$ in water, or in pyridine/ROH, wherein the R in ROH is an alkyl, aralkyl or aryl group having 1–10 carbon atoms.

9. A method for synthesizing an oligonucleotide comprising:
sequentially coupling one or more monomer synthons according to claim 1 to a nucleoside to produce a base-protected oligonucleotide, wherein the R in the monomer synthon is a phosphoramidite, and then
deprotecting the base-protected oligonucleotide with a chemoselective agent comprising $Br_2$ or $I_2$ in water, or in pyridine/ROH, wherein the R in ROH is an alkyl, aralkyl or aryl group having 1–10 carbon atoms.

10. The method according to claim 9, wherein the R in ROH is a methyl group.

11. The method of claim 9, wherein D is a dimethoxytrityl group.

12. The method of claim 9, wherein the method is conducted in a solution phase or a solid phase.

13. The method of claim 9, wherein the nucleoside is a monomer or a terminal nucleoside of an oligonucleotide chain.

14. The monomer synthon according to claim 1, wherein R is a phosphotriester group.

15. A method for synthesizing an oligonucleotide comprising:
sequentially coupling a monomer synthon according to claim 1, to a nucleoside to produce a base-protected oligonucleotide, wherein the R in the monomer synthon is a phosphoramidite, and then
simultaneously oxidizing the internucleoside linkages and deprotecting the base-protected oligonucleotide with a chemoselective agent comprising $Br_2$ or $I_2$ in water, or in pyridine/ROH, wherein the R in ROH is an alkyl, aralkyl or aryl group having 1–10 carbon atoms.

16. A method for synthesizing an oligonucleotide comprising:
sequentially coupling a monomer synthon according to claim 1 to a nucleoside to produce a base-protected oligonucleotide, wherein the R in the monomer synthon is a phosphotriester, and then
deprotecting the base-protected oligonucleotide with a chemoselective agent comprising $Br_2$ or $I_2$ in water, or in pyridine/ROH, wherein the R in ROH is an alkyl, aralkyl or aryl group having 1–10 carbon atoms.

17. The method according to claim 16, wherein the R in ROH is a methyl group.

18. The method of claim 16, wherein D is a dimethoxytrityl group.

19. The method of claim 16, wherein the method is conducted in a solution phase or a solid phase.

20. The method of claim 16, wherein the nucleoside is a monomer or a terminal nucleoside of an oligonucleotide chain.

21. The monomer synthon according to claim 1, wherein D is a dimethoxytrityl group or a trityl group.

22. A method for synthesizing an oligonucleotide comprising:
sequentially coupling a monomer synthon according to claim 1 to a nucleoside to produce a base-protected oligonucleotide, wherein the R in the monomer synthon is a phosphotriester, and then
simultaneously oxidizing the internucleoside linkages and deprotecting the base-protected oligonucleotide with a chemoselective agent comprising $Br_2$ or $I_2$ in water, or in pyridine/ROH, wherein the R in ROH is an alkyl aralkyl or aryl group having 1–10 carbon atoms.

23. A method for synthesizing an oligonucleotide comprising:
sequentially coupling together two or more monomer synthons according to claim 1 to produce a base-protected oligonucleotide, and then
deprotecting the base-protected oligonucleotide with a chemoselective agent or a non-chemoselective agent to produce the oligonucleotide.

24. The method of claim 23, wherein the deprotecting step is conducted with a chemoselective agent that comprises a halogen in water, or in pyridine/ROH, wherein R is an alkyl, aralkyl or aryl group having 1–10 carbon atoms.

25. The method of claim 24, wherein the halogen is $Br_2$ or $I_2$, and wherein R is methyl.

26. A method for synthesizing an oligonucleotide comprising:
   sequentially coupling one or more monomer synthons according to claim 1 to a nucleoside that is covalently bound to a suitable solid support to produce a base-protected oligonucleotide that is covalently bound to the suitable solid support, and then
   deprotecting the base-protected oligonucleotide with a chemoselective agent or a non-chemoselective agent to produce the oligonucleotide that is covalently bound to the suitable solid support.

27. The method according to claim 26, wherein the suitable solid support is a controlled-pore glass.

28. The method of claim 26, wherein the deprotecting step is conducted with a chemoselective agent that comprises a halogen in water, or in pyridine/ROH, wherein R is an alkyl, aralkyl or aryl group having 1–10 carbon atoms.

29. The method of claim 28, wherein the halogen is $Br_2$ or $I_2$, and wherein R is methyl.

30. The method of claim 26, further comprising oxidizing the internucleoside linkages of the oligonucleotide prior to deprotecting the base-protected oligonucleotide to produce an unprotected oligonucleotide that is covalently bound to the suitable solid support.

31. The monomer synthon according to claim 1, wherein R is a phosphoramidite group.

32. The monomer synthon according to claim 17, wherein the phosphoramidite group is a cyclic phosphoramidite group.

33. A method for synthesizing an oligonucleotide comprising:
   sequentially coupling the monomer synthon of claim 1 to a nucleoside to produce a base-protected oligonucleotide, and then
   deprotecting the base-protected oligonucleotide with a chemoselective agent or a non-chemoselective agent to produce the oligonucleotide.

34. The method of claim 7, wherein the method is conducted in a solution phase or a solid phase.

35. The method of claim 7, wherein the nucleoside is a monomer or a terminal nucleoside of an oligonucleotide chain.

36. The method of claim 7, wherein the deprotecting step is conducted with a chemoselective agent that comprises a halogen in water, or in pyridine/ROH, wherein R is an alkyl, aralkyl or aryl group having 1–10 carbon atoms.

37. The method of claim 11, wherein the halogen is $Br_2$ or $I_2$, and wherein R is methyl.

* * * * *